United States Patent
Eckstein et al.

(10) Patent No.: US 8,772,567 B2
(45) Date of Patent: Jul. 8, 2014

(54) USE OF A POLYURETHANE FOAM AS A WOUND DRESSING IN NEGATIVE PRESSURE THERAPY

(75) Inventors: Axel Eckstein, Heidenheim (DE); Pierre Croizat, Herbrechtingen (DE); Ulrich Fink, Heidenheim (DE); Krzysztof-Daniel Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 276 days.

(21) Appl. No.: 13/213,214

(22) Filed: Aug. 19, 2011

(65) Prior Publication Data

US 2012/0046588 A1    Feb. 23, 2012

Related U.S. Application Data

(60) Provisional application No. 61/375,085, filed on Aug. 19, 2010.

(51) Int. Cl.
    *A61F 13/00*       (2006.01)

(52) U.S. Cl.
    USPC ............................. 602/46; 604/269; 604/304

(58) Field of Classification Search
    USPC ......... 602/46, 41–43; 604/304–308, 289, 290
    See application file for complete search history.

(56) References Cited

U.S. PATENT DOCUMENTS

| | | | |
|---|---|---|---|
| 3,572,340 A | 3/1971 | Lloyd et al. | |
| 3,610,238 A | 10/1971 | Rich, Jr. | |
| 3,911,922 A | 10/1975 | Kliger | |
| 4,812,368 A * | 3/1989 | Scherzer et al. | 428/332 |
| 5,636,643 A | 6/1997 | Argenta et al. | |
| 5,645,081 A | 7/1997 | Argenta et al. | |
| 6,071,267 A | 6/2000 | Zamierowski | |
| 2004/0030304 A1* | 2/2004 | Hunt et al. | 604/317 |
| 2007/0161936 A1 | 7/2007 | Svetlik | |
| 2007/0238797 A1 | 10/2007 | Addison et al. | |
| 2009/0018480 A1 | 1/2009 | Mager et al. | |
| 2011/0196329 A1 | 8/2011 | Eckstein et al. | |
| 2011/0313383 A1* | 12/2011 | Hofstetter et al. | 604/372 |
| 2012/0046589 A1 | 2/2012 | Eckstein et al. | |

FOREIGN PATENT DOCUMENTS

| | | |
|---|---|---|
| GB | 2462004 A | 1/2010 |
| WO | 94/20041 | 9/1994 |
| WO | 2009/126102 A1 | 10/2009 |
| WO | 2010/046095 A1 | 4/2010 |
| WO | 2011/049522 A1 | 4/2011 |

* cited by examiner

*Primary Examiner* — Kim M Lewis
(74) *Attorney, Agent, or Firm* — Jason D. Voight

(57) ABSTRACT

A device for negative pressure wound therapy having a cover material for air-tight sealing of the wound space connected to a negative pressure source; and a wound dressing having an open-cell polyurethane foam. The open-cell polyurethane foam has special properties, in particular a tensile strength after three days of storage in bovine serum, measured in accordance with DIN 53571, between 80 kPa and 300 kPa. The open-cell polyurethane foam may be used as a wound dressing in negative pressure wound therapy.

20 Claims, 3 Drawing Sheets

USE OF A POLYURETHANE FOAM AS A WOUND DRESSING IN NEGATIVE PRESSURE THERAPY

This application claims priority to U.S. Provisional Application Ser. No. 61/375,085, filed Aug. 19, 2010, the disclosure of which is incorporated by reference herein.

BACKGROUND OF THE INVENTION

The invention relates to a device for negative pressure wound therapy comprising (a) a cover material for air-tight sealing of the wound space; (b) as applicable a means for the connection of a negative pressure source and (c) a wound dressing comprising an open-cell polyurethane foam, whereby the open-cell polyurethane foam has special characteristics, in particular a tensile strength after three days of storage in bovine serum, measured in accordance with DIN 53571, between 80 kPa and 300 kPa. The invention further relates to the use of said an open-cell polyurethane foam as a wound dressing in negative pressure wound therapy.

A wound is defined as the separation of the coherence of tissues of the outer body of humans or animals. It can result in a loss of substance.

Devices for the negative pressure wound therapy are known in the prior art. For example WO 1993/009727 A1 describes a device to promote healing of the wound by the application of a negative pressure on the skin area which is wounded and the area surrounding the wound. The device according to WO 1993/009727 A1 comprises a negative pressure device to generate the negative pressure, an air-tight cover of the wound which has a functional connection with the negative pressure device, as well as a wound dressing for positioning on the wound inside the air-tight cover.

Devices for the negative pressure wound therapy are commercially available, for example the V.A.C.® device from the company KCI. Commercially available devices often use a wound dressing which contains an open-cell polymer foam such as polyvinyl alcohol (PVA) or polyurethane (PU).

The commercially available foam dressings are compressed to a different degree, depending on the negative pressure applied. This can cause a constriction of the passages necessary for the removal of the wound exudate. Adhesion of the foam with the wound can also occur. Newly formed tissue can grow into the wound. This problem is a familiar complication in the negative pressure therapy of wounds (FDA complaint data base). In order to solve this problem, additional wound contact layers are often introduced between the foam and the wound, for example a film (see, for example, WO2001/85248). However, these additional wound contact layers can reduce the passage of wound exudate.

When the wound dressing is to be changed, elaborate measures have to be taken to remove adhered foam, for example by rinsing with Ringer's solution. Tissue which has grown into the foam can lead to a tissue traumatization when the wound dressing is removed and thus delay the healing process.

When conventional wound dressings are used, particles of foam can also enter the wound. These can irritate the wound and delay the healing process. This problem is aggravated if the wound dressing is cut to the size of the wound before being applied, as this results, in particular, in loose foam particles at the cut edges.

BRIEF SUMMARY OF THE INVENTION

It is the object of the present invention to further improve negative pressure wound therapy and to overcome the disadvantages of the prior art. The invention provides devices and methods for negative pressure wound therapy, with which a therapy can be carried out as effectively and gently as possible. In particular, the invention is aimed at preventing the build-up of foam particles in the wound.

Unexpectedly, the objects could be solved by the use of a wound dressing comprising a special polyurethane foam. In particular, it was found that it was possible to simulate the conditions prevailing in negative pressure therapy by the storage of the polyurethane foam in bovine serum. If the polyurethane foam is selected in such a way that after three days of storage in bovine serum it has an advantageous tensile strength, this leads to a surprisingly sharp reduction of undesired foam particles in the wound. It was also found that it is possible to obtain polyurethane foams which solve the aforementioned objects unexpectedly advantageously if certain other physical parameters are present and the starting materials are appropriately selected.

DETAILED DESCRIPTION OF THE INVENTION

Figure 1:
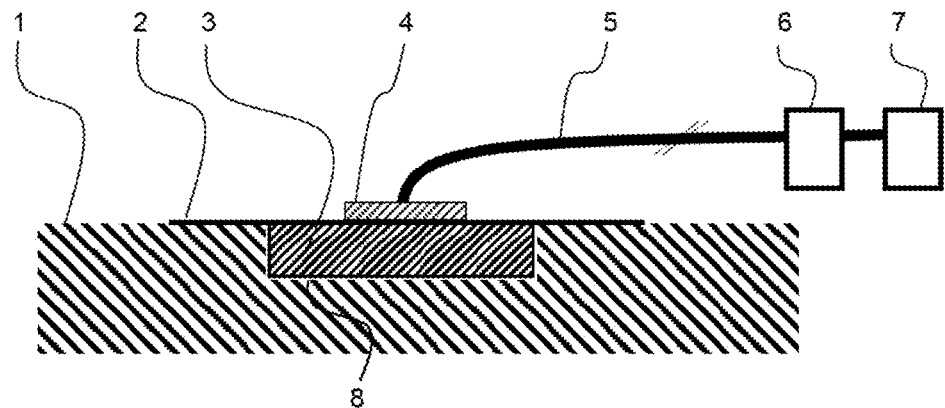
FIG. 1 shows a schematic view (side view) of the device in accordance with the present invention.

The object of a first aspect of the invention is, therefore, a device for negative pressure wound therapy comprising
(a) a cover material for air-tight sealing of the wound space;
(b) as applicable, a means for the connection of a negative pressure source; and
(c) an open-cell polyurethane foam as a wound dressing, obtainable by reaction of a mixture comprising the components
(i) polyisocyanate,
(ii) polyol, in particular polyester polyol,
(iii) blowing agent, and
(iv) catalyst,
whereby the open-cell foam, after three days of storage in bovine serum, preferably has a tensile strength, measured in accordance with DIN 53571, between 80 kPa and 300 kPa.

The object of a second aspect of the invention is, therefore, a device for negative pressure wound therapy comprising
(a) a cover material for air-tight sealing of the wound space;
(b) as applicable, a means for the connection of a negative pressure source; and
(c) an open-cell polyurethane foam as a wound dressing, obtainable by reaction of a mixture comprising the components
(i) polyisocyanate,
(ii) polyol, in particular polyester polyol,
(iii) blowing agent, and
(iv) catalyst, whereby the open-cell polyurethane foam preferably has an air permeability of 1,000 to 8,000 l/(m²sec), measured in accordance with DIN EN ISO 9237.

The object of a third aspect of the invention is, therefore, a device for negative pressure wound therapy comprising
(a) a cover material for air-tight sealing of the wound space;
(b) as applicable, a means for the connection of a negative pressure source; and
(c) an open-cell polyurethane foam as a wound dressing, obtainable by reaction of a mixture comprising the components
(i) polyisocyanate, selected from MDI, PMDI, TDI and/or HDI,
(ii) polyester polyol, which is preferably obtainable by reaction of a dicarboxylic acid with 4 to 8 carbon atoms with a dialcohol with 2 to 6 carbon atoms, and/or preferably has a weight average molecular weight of 500 to 4.000 g/mol,
(iii) blowing agent, and
(iv) catalyst.

The invention also includes any combinations of the cited aspects.

A further object of the invention is the use of the open-cell polyurethane foam (c) described above in the three aspects, e.g. the use of an open-cell polyurethane foam which has a tensile strength after three days of storage in bovine serum, measured in accordance with DIN 53571, between 80 kPa and 300 kPa, as a wound dressing for or in negative pressure wound therapy.

The new device in accordance with the present invention or the use of the wound dressing in accordance with the present invention is distinguished by several unexpected advantages.

In particular, by selection of the characteristics of the foam it was possible to advantageously reduce the number of undesirable particles entering the wound.

The use of the wound dressing in accordance with the present invention also improved the atraumatic characteristics so that a negative pressure therapy was possible without additional wound contact layers.

The wound dressing in accordance with the present invention allows adequate drainage of wound exudates, feels relatively pleasant and thus leads to an increase in patient compliance (observance of the therapy instructions by the patient).

The components (a) to (c) of the device in accordance with the present invention are described in the following.

The device in accordance with the present invention comprises a cover material (a) for air-tight sealing of the wound space. The wound space is regarded as the wound and the area surrounding the wound. "Air-tight sealing" does not mean that there is no exchange of gas between the wound space and its surroundings. Rather, "air-tight sealing" in this context means that, taking into account the vacuum pump used, the negative pressure necessary for the negative pressure wound therapy can be maintained. This means that cover materials can also be used which have a slight degree of gas permeability as long as the negative pressure necessary for the negative pressure wound therapy can be maintained.

In a preferred embodiment of the invention, the cover material for the air-tight sealing of the wound includes a water-insoluble polymer, or a metal foil. The cover material preferably has a thickness of 10 µm to 10,000 µm, in particular from 25 µm to 100 µm.

In a preferred embodiment of the invention, the cover material (a) is a water-insoluble polymer. Preferably the water-insoluble polymer has a solubility of 10 mg/l or less, more preferably of 1 mg/ml or less, particularly from 0.0001 to 1 mg/ml (determined in accordance with the column elution method pursuant to EU Directive RL67-548EEC, Annex V, Chapter A6). Examples include polyurethane, polyester, polypropylene, polyethylene, polyamide or polyvinyl chloride, polyorganosiloxane (silicone), or a mixture thereof. The cited polymers are preferably provided in non-cellular form.

It has been demonstrated that the objects explained at the beginning can be solved in a particularly advantageous manner using a cover material with a specific water vapor permeability. In a preferred embodiment, the cover material thus has a water vapor permeability of 100 to 2,500 g/m²×24 h, more preferably from 500 to 2,000 g/m²×24 h, and even more preferably from 800 to 1,600 g/m²×24 h, in particular from 1,050 to 1,450 g/m²×24 h, determined in accordance with DIN EN 13726-2 at 23° C. and 85% relative humidity. In particular, the combination of a cover film (a) having the aforementioned water vapor permeability with an open-cell polyurethane foam having the physical properties described below is particularly advantageous.

The device in accordance with the present invention for negative pressure wound therapy comprises a means (b) for the connection of a negative pressure source, i.e. a means for the generation of a negative pressure in the wound space. In a preferred embodiment, this is a means (b) for the functional connection of the wound space with a negative pressure source outside of the cover material so that a negative pressure can be generated in the wound space and fluids can be sucked out of the wound space.

The expression "negative pressure in the wound space" in the context of the invention describes an air pressure which is lower inside the wound dressing compared to the atmospheric pressure. "Within the wound dressing" refers to the cavity formed between the cover material and the wound.

The pressure difference between the air pressure inside the wound dressing and the atmospheric pressure is stated in the context of the invention in mm Hg (millimeters of mercury), as this is the convention in negative pressure therapy. 1 mm Hg corresponds to one torr or 133.322 Pa (Pascal). In the context of the invention, the negative pressure, i.e. the pressure difference between the pressure inside the wound dressing and the atmospheric pressure, is stated as a positive numerical value in mm Hg.

In one embodiment of the invention, the negative pressure is at least 25 mm Hg up to a maximum of 250 mm Hg, preferably at least 50 mm Hg up to a maximum of 150 mm Hg. This negative pressure range has proved suitable for wound healing. In a preferred embodiment of the invention, the negative pressure is at least 80 mm Hg up to a maximum of 140 mm Hg, more preferably at least 120 mm Hg up to a maximum of 130 mm Hg.

The device in accordance with the present invention for negative pressure wound therapy preferably comprises, as set out above, a means (b) for connection of a negative pressure source, i.e. a means for the functional connection of the wound space with a negative pressure source outside of the cover material.

The functional connection can be generated, for example, by a connection line or by a negative pressure connector. Negative pressure connectors are known to those skilled in the art as "ports".

In one embodiment, the means (b) is a connection line, preferably a tube, in particular a silicone drainage tube. The connection line can be ducted through the cover material. Alternatively, the at least one connection line can be led under the edge of the cover material. In both cases the penetration point must be sealed air-tight so that the desired negative pressure can be maintained in the dressing.

In a further preferred embodiment, the means (b) is a negative pressure connector (port) which can be fastened to one of the inner or outer sides of the cover material, whereby the cover material has the corresponding openings. In this embodiment it is also important to ensure air-tight sealing either of the penetration opening (inside port) or the surface of the dressing (outside port). Sealing can be achieved, for example, with an adhesive foil, an adhesive paste or an adhesive strip.

Alongside the components (a) and, optionally, (b) described above, the device in accordance with the present invention also has a component (c). The wound dressing (c) used in the device in accordance with the present invention is described in more detail in the following. All of the explanations on the wound dressing (c) refer not only to the device in accordance with the present invention, but also to the method in accordance with the present invention for the manufacture of the wound dressing and the use in accordance with the present invention of the wound dressing in negative pressure wound therapy.

The wound dressing (c) comprises of an open-cell polyurethane foam (PUR foam). Foams are usually materials with cells (open, closed, or both) distributed over their whole mass. Such materials thus usually have a raw density (in accordance with DIN EN ISO 845), which is lower than the density of the basic substance.

A cell is an individual cavity formed in the manufacture of the foam which is partially or fully enclosed by the cell walls and/or cell struts.

A closed cell is usually a cell which is completely enclosed by its walls and has no connection via the gas phase with the other cells. An open cell is usually a cell which is connected with other cells via the gas phase. In the context of this application, the term open-cell means that in the polyurethane foam there is at least 60% open cells, preferably at least 90% open cells, even more preferably 98% open cells, in particular essentially 100% open cells relative to the total number of cells. The open cell content of the polyurethane foam is usually determined in accordance with ASTM D 2856-87, procedure B.

The cell wall is usually taken to mean the wall enclosing the cell. The cell wall can also be referred to as the cell membrane. The cell strut is usually taken to mean the area of the cell wall which separates more than two cells. Cell struts are preferably at least 1.5 times the thickness, even more preferably at least twice the thickness of the rest of the cell wall.

The open-cell polyurethane foam can be a reticulated foam or a non-reticulated foam. A reticulated foam is taken to mean a foam which consists largely of cell struts. In a reticulated foam, therefore, the cell walls are largely absent. The reticulation is usually carried out in a pressure chamber, e.g. a steel chamber. When the foam is introduced to the steel chamber, the air is sucked out (preferably from 50 to 100 weight percent, more preferably from 70 to 99 weight percent) and replaced by a combustion gas mixture, preferably by a mixture containing hydrogen and oxygen, in particular in a molar ratio of 2:1. When the gas mixture is ignited, the cell skins are torn by the resulting heat and the pressure wave. There may also be at least a partial melting of the cell struts so that these are reinforced.

The foam (c1) usually has a cell number (=number of pores along a straight line per cm) of 3 to 40 $cm^{-1}$, preferably 5 to 25 $cm^{-1}$, more preferably 7 to 18 $cm^{-1}$, even more preferably from 8 to 15 $cm^{-1}$. The cell number is preferably determined by microscope.

In principle, the open-cell polyurethane should fulfill certain physical requirements. It has been demonstrated that the objects set out above can be solved unexpectedly advantageously if the polyurethane foam has a specific tensile strength, a specific ductile yield and/or a specific hardness.

In accordance with the present invention, the polyurethane foam usually has a tensile strength after three days of storage in bovine serum between 80 kPa and 300 kPa, preferably between 110 kPa and 250 kPa, more preferably between 120 kPa and 230 kPa, even more preferably from 130 to 220 kPa, especially preferably from 140 to 200 kPa, very especially preferably from 155 to 190 kPa and in particular from 160 to 185 kPa.

Bovine serum is known in the prior art. This is a serum gained from bovine blood. Preference is given to the use of the "Standard Fetal Bovine Serum" sold under the trade name of HyClone® by the company Thermo Scientific. In a preferred embodiment, the bovine serum used essentially has the following composition and properties:

| Protein content and other values | |
|---|---|
| Albumin | 1.9 gm/dl |
| Alkaline phosphatase | 213 mU/ml |
| Blood urea nitrogen | 12 mg/dl |
| Creatinine | 2.77 mg/dl |
| Gamma globulin | 1.7% tp |
| Blood sugar (glucose) | 107 mg/dl |
| Glutamic oxaloacetic transaminase (SGOT) | 152 mU/ml |
| Glutamic pyruvic transaminase (SGPT) | 37 mU/ml |
| IgG - nephelometer | 0.14 mg/ml |
| Lactate dehydrogenase | 2,479 mU/ml |
| Osmolality | 312 mOsm/kg |
| pH | 7.18 |
| Total bilirubin | 0.4 mg/dl |
| Total protein | 3.7 gm/dl |
| Content of trace elements and iron | |
| Calcium | 13.1 mg/dl |
| Chloride | 99 mEq/l |
| Inorganic phosphorus | 9.6 mg/dl |
| Iron | 160 µg/dl |
| Saturation concentration (iron) | 79% |
| Potassium | >10.0 mEq/l |
| Sodium | 133 mEq/l |
| Total iron-binding capacity (TIBC) | 201 µg/dl |

The specimen to be measured is placed in bovine serum and immersed for 3 days at 23° C. Then the tensile strength is determined in accordance with DIN 53571. In the context of this application, the expression "in accordance with DIN 53571" means that the tensile strength is determined in accordance with this standard in principle, whereby, in deviation from the standard, the specimen immersed for three days in bovine serum is not completely dried out. Instead, the specimen is taken from the bovine serum and immersed in 1 liter of water to be rinsed. Then the test body is squeezed out with cellulose paper. Also, in deviation from the standard, a rectangular test body is used with the dimensions 10×12.5×75.

The tensile strength is measured by using a tensile strength testing device in accordance with EN ISO 527-1 [April 1996] by the company Zwick (Ulm). The following test parameters apply:
Test speed: 500 mm/min
Clamping length: 50 mm
Initial load: 0.1 N
Specimen width b0: 12.5 mm Furthermore, the polyurethane foam (c) preferably has a ductile yield of 150% to 700%, more preferably from 200% to 650%, even more preferably from 240% to 340%, particularly 260% to 320%, measured in accordance with DIN 53571 (Procedure 1, body A). In addition to this, the polyurethane foam preferably has a hardness of 20 to 70 Shore A, more preferably from 30 to 60 Shore A, even more preferably from 40 to 50 Shore A, measured in accordance with DIN 53505, whereby the measurement was taken at 23° C. on a slab-like, flat and smooth test body with a thickness of 6 mm.

It has also been demonstrated that the objects set out above can be solved unexpectedly advantageously if the polyurethane foam has a specific air permeability. In a preferred embodiment the polyurethane foam has an air permeability of 1,000 to 8,000 l/(m²sec), more preferably from 1,500 to 6,000 l/(m²sec), even more preferably from 2,000 to 5,000 l/(m²sec), especially preferably from 2,300 to 4,000 l/(m²sec), and in particular from 2,400 to 3,300 l/(m²sec) measured in accordance with DIN EN ISO 9237 (20 mm test thickness, 20 cm² test area, 200 Pa differential pressure).

It has also been demonstrated that the objects set out above can be solved unexpectedly advantageously if the polyurethane foam displays visco-elastic behavior. This means that the behavior of the polyurethane foam under strain looks like a combination of an elastic solid and a viscous fluid. The visco-elastic behavior can be characterized by a torsional vibration test in accordance with DIN 53445, Procedure A. It is preferred that the foam, when determined in accordance with DIN 53445, Procedure A at 23° C., has a mechanical loss factor of 0.1 to 1.0, more preferably from 0.15 to 0.8, even more preferably from 0.2 to 0.6.

It has also been demonstrated that the objects set out above can be solved unexpectedly advantageously if the foam (c) has a raw density between 15 and 55 kg/m³, more preferably between 20 and 35 kg/m³, even more preferably between 22 and 30 kg/m³, in particular between 24 and 28 kg/m³, measured in accordance with DIN EN ISO 845 (test body with dimensions 100 mm×100 mm×50 mm, conditioning for 24 h in a standard climate (23° C., 50% relative humidity, 1013 mbar)).

Insofar as the relevant standards do not state otherwise, the tests are generally carried out at 23° C. and 50% relative humidity and at a pressure of 1013 mbar.

Preferred embodiments of the usable polyurethane foams (c-PUR) are explained below. The polyurethane foam is usually obtained by reaction of a curable mixture comprising the components (i-PUR) polyisocyanate,
(ii-PUR) compounds reactive to isocyanate, in particular polyol,
(iii-PUR) catalyst,
(iv-PUR) blowing agent, and
(v-PUR) additives, as applicable.

Generally known aliphatic, cycloaliphatic and/or, in particular, aromatic polyisocyanates can be used as isocyanates (i-PUR). For example, diphenylmethane diisocyanate (MDI), in particular, 4,4'-diphenylmethane diisocyanate (4,4'-MDI), mixtures of monomeric diphenylmethane diisocyanates and higher-nucleus homologues of diphenylmethane diisocyanate (polymeric MDI), tetramethylene diisocyanate (TMDI), hexamethylene diisocyanate (HDI), toluoylene diisocyanate (TDI) or mixtures thereof can be used to produce the polyurethanes.

Preference is given to MDI, in particular 4,4'-MDI and/or HDI. The preferably used 4,4'-MDI can contain small quantities, up to around 10 weight percent, of allophanate or uretonimine-modified polyisocyanates. Small quantities of polyphenylene polymethylene polyisocyanate (PMDI) can also be used. The total quantity of these PMDI should not exceed 5 weight percent of the isocyanate used.

The polyisocyanate component (i-PUR) is preferably used in the form of polyisocyanate prepolymers. These polyisocyanate prepolymers are obtainable by reaction of the polyisocyanates described above (I-PUR), for example at temperatures of 30 to 100° C., preferably at around 80° C., with a substoichiometric amount of the polyols (ii-PUR) described below to form a prepolymer. The polyol-polyisocyanate ratio is selected in such a way that the NCO content of the prepolymer is 8 to 28 weight percent, preferably 14 to 26 weight percent, particularly preferably 17 to 23 weight percent.

Polyols such as polyetherols and/or polyesterols are usually used as compounds reactive to isocyanates (ii-PUR).

It is also possible to use polyether polyalcohols (referred to in this application as "polyether polyols") with an OH functionality of 1.9 to 8.0, a hydroxyl number of 50 to 1,000 mg KOH/g and, as applicable, 10 to 100% primary hydroxyl groups. These types of polyether polyols are known, commercially available and based, for example, on starter compounds which can be reacted with alkylene oxides, for example propylene oxide and/or ethylene oxide, under generally known conditions. The content of primary hydroxyl groups can be achieved by eventually reacting the polyols with ethylene oxide. To produce the open-cell foam (c) it is preferable not to use polyether polyols.

Preference is given to the use of polyester polyols in the component (ii-PUR). The polyesterols (ii-PUR) are generally produced by condensation of multifunctional alcohols, preferably diols, with 2 to 12 carbon atoms, preferably 2 to 6 carbon atoms, with multifunctional carboxylic acids with 2 to 12 carbon atoms, preferably 4 to 8 carbon atoms. Examples of suitable acids include succinic acid, glutaric acid, adipic acid, phthalic acid, isophthalic acid and/or terephthalic acid and mixtures thereof. Adipic acid is especially preferred. Examples of suitable di- and multi-valent alcohols include ethanediol, diethylene glycol, 1,4-butanediol, 1,5-pentanediol, and/or 1,6-hexanediol and mixtures thereof. 1,4-butanediol is especially preferred.

The reaction conditions of carboxylic acid and alcohol are usually selected in such a way that the resulting polyesterols do not have any free acid groups. The resulting polyesterols also generally have a weight average molecular weight (determined using gel permeation chromatography) of 500 to 3,500 g/mol, preferably of more than 1,000 g/mol to 3,000 g/mol, in particular from 1,500 to 2,500 g/mol. In general, the polyesterols used have an average theoretical functionality of 2.0 to 4, preferably of more than 2 to less than 3. The polyesterols used also generally have an average OH number of 20 to 150, preferably from 30 to 80.

In a preferred embodiment, the polyesterols used have a viscosity of 150 mPa·s to 600 mPa·s, preferably from 200 mPa·s to 550 mPa·s, more preferably from 220 mPa·s to 500 mPa·s, especially preferably from 250 mPa·s to 450 mPa·s and in particular from 270 mPa·s to 350 mPa·s, measured in accordance with DIN 53 015 at 75° C.

The compounds (ii-PUR) can be mixed with chain extenders and/or cross-linking agents. The chain extenders are mainly 2-functional alcohols with molecular weights from 60 to 499, for example ethylene glycol, propylene glycol, butanediol-1,4, pentanediol-1,5, dipropylene glycol and/or tripropylene glycol. The cross-linking agents are compounds with molecular weights from 60 to 499 and 3 or more active H atoms, preferably amines, and especially preferably alcohols, for example glycerin, trimethylol propane and/or pentaerythrite.

In a preferred embodiment the component (ii-PUR) preferably contains (or consists of) 0 to 25 weight percent, preferably 1 to 20 weight percent, chain extenders and/or cross-linking agents and 75 to 100 weight percent, preferably 80 to 99 weight percent polyol(s), in particular polyester polyol(s), relative to the total weight of the component (ii-PUR).

Compounds which accelerate the reaction of the component (i-PUR) with the component (ii-PUR) can be used as catalysts (iii-PUR). These could include, for example, tertiary amines and/or organo-metallic compounds, in particular tin compounds. The following compounds can be used, for example, as catalysts: triethylene diamine, aminoalkyl and/or aminophenyl imidazoles and/or tin (II) salts of organic carboxylic acids. Catalysts are generally used in a quantity of 0.1 to 5 weight percent relative to the weight of the component (ii-PUR).

Generally known chemically or physically active compounds can be used as blowing agents (iv-PUR). Water can be used preferably as a physically active blowing agent, which, when reacted with the isocyanate groups, forms carbon dioxide. Examples of physical blowing agents include (cyclo) aliphatic hydrocarbons, preferably those with 4 to 8, especially preferably 4 to 6, and in particular 5 carbon atoms, partially halogenated hydrocarbons or ethers, ketones or acetates. The amount of blowing agents used depends on the desired density of the foams. The different blowing agents can be used individually or in any mixture with each other. Special preference is given to the use of only water as a blowing agent, generally in a quantity of 0.1 to 5 weight percent, in particular from 2.5 to 4 weight percent relative to the weight of the component (ii-PUR). Physical blowing agents are preferably used in a quantity of <0.5 weight percent relative to the weight of the component (ii-PUR).

The reaction takes place as applicable in the presence of (v-PUR) auxiliaries and/or additives, for example fillers, cell regulators, cell openers, surfactants, and/or stabilizers against oxidative, thermal or microbial decomposition or ageing.

To produce polyurethane foams, the components (i-PUR) and (ii-PUR) are generally made to react with each other in such quantities that the equivalence ratio of NCO groups to the sum of the reactive hydrogen atoms (in particular to the sum of the OH groups) is 1:0.8 to 1:1.25, preferably 1:0.9 to 1:1.15. A ratio of 1:1 corresponds here to an NCO index of 100. The desired open cell content of the polyurethane foam is generally achieved by a suitable selection as recognized by those skilled in the art of the components (i-PUR) to (v-PUR). As applicable, after setting the resulting PUR foam is reticulated. For more information on this, reference is made to the explanations given above.

It has also been demonstrated that the objects set out above can be solved unexpectedly advantageously if the polyurethane foam (c) contains silver in the form of silver ions or in the form of atomic silver. Preferably, a silver coating is applied after production of the polyurethane foam. Alternatively the silver can be added to the curable composition. Preferably, the polyurethane foam contains 0.000001 to 0.1 weight percent, more preferably 0.0001 to 0.01 weight percent silver relative to the total weight of the polyurethane foam.

It has also been shown that the objects described at the beginning could not always be solved satisfactorily with polyurethanes solely on the basis of aliphatic starting materials. Rather, the use of aromatic structural components (i-PUR and/or ii-PUR) proves advantageous. In a preferred embodiment the polyurethane foam (c) thus has a proportion of aromatic compounds of 5 to 50%, more preferably from 10 to 45%, in particular from 15 to 40%. The proportion of aromatic compounds is determined by the ratio of the weight of aromatic rings to the total weight of the foam.

In a preferred embodiment of the invention, the open-cell polyurethane foam has a thickness of 1 to 50 mm, in particular from 15 to 35 mm.

The open-cell polyurethane foam can also be used in a dry condition soaked with an ointment base, in particular a triglyceride ointment base. An especially preferred ointment base contains:

20 to 90 weight percent, preferably 55 to 80 weight percent triglycerides, in particular containing fatty acid residues selected from caprylic acid, capric acid, lauric acid and/or stearic acid;

5 to 75 weight percent, preferably 15 to 45 weight percent triglycerides, in particular containing fatty acid residues selected from isostearic acid, stearic acid, 12-hydroxy-stearic acid and/or adipic acid; and 0 to 30 weight percent, preferably 5 to 20 weight percent polyethylene glycol with a weight average molecular weight of 500 to 3,000 g/mol. In a preferred embodiment the proportion of ointment base is 10 to 95 weight percent, more preferably 30 to 92 weight percent, even more preferably 45 to 90 weight percent, especially preferably 55 to 88 weight percent, in particular 65 to 85 weight percent relative to the total weight of the foam and the ointment base.

The foam is preferably not soaked, for example, with an activation solution (e.g. Ringer's solution). It is also preferred that the open-cell polyurethane foam is not coated or impregnated with a silicone gel, e.g. a hydrophobic silicone gel.

The polyurethane foam can also contain substances with antimicrobial action. Substances with antimicrobial action can include for example, substances with amino or imino groups. Substances with antimicrobial action can also be antimicrobially active metal cations, in particular silver cations, for example a complex of 1-vinyl-2-pyrrolidones with silver cations. Other especially suitable substances with antimicrobial action further include biguanide derivatives such as chlorhexidine or polybiguanides such as polyethylene biguanide (PEB), polytetramethylene biguanide (PTMB) or polyethylene hexamethylene biguanide (PEHMB). An especially preferred polybiguanide is polyhexamethylene biguanide (PHMB or polyhexanide). Other suitable substances with antimicrobial action are polyguanidines such as polyhexamethylene guanidine (PHMG), N-octyl-1-[10-(4-octylimi-nopyridine-1-yl)decyl]pyridine-4-imine (octenidine), quaternary ammonium compounds such as benzalkonium chloride or cetylpyridinium chloride, triazines such as 1-(3-chloroallyl)-3,5,7-triaza-1-azonia-adamantan-chloride or the ammonium compound taurolidine.

Preferably the open-cell polyurethane foam is impregnated or coated with the aforementioned substances with antimicrobial action.

Substances with antimicrobial action are usually contained in the polyurethane foam in a quantity of 0 to 30 weight percent, preferably from 0.1 to 15 weight percent relative to the total weight of the polyurethane foam.

In principle, the explanations of preferred embodiments of individual parameters of the polyurethane foam (c) must not be seen in isolation, but in combination with the explanations of preferred embodiments of other parameters or in combination with the explanations of the substance compositions. Accordingly, the device in accordance with the present invention and its use in accordance with the present invention can be an open-cell foam (c) which, after three days of storage in bovine serum, has a tensile strength of 80 kPa to 300 kPa, preferably from 110 kPa to 250 kPa, more preferably from 120 kPa to 230 kPa, even more preferably from 130 kPa to 220 kPa, especially preferably from 140 kPa to 200 kPa, most especially preferably from 155 kPa to 190 kPa and in particular from 160 kPa to 185 kPa; a ductile yield of 150% to 500%, more preferably from 200% to 380%, even more preferably from 240% to 340%, in particular 260% to 320%; a mechanical loss factor of 0.1 to 1.0, more preferably from 0.15 to 0.8, even more preferably from 0.2 to 0.6;
a hardness of 20 to 70 Shore A, more preferably from 30 to 60 Shore A, even more preferably from 40 to 50 Shore A;
a cell number (=number of pores along a straight line per cm) from 3 to 40 $cm^{-1}$, preferably from 5 to 25 $cm^{-1}$, more preferably from 7 to 18 $cm^{-1}$, even more preferably from 8 to 15 $cm^{-1}$;
a raw density between 15 and 55 $kg/m^3$, more preferably between 20 and 35 $kg/m^3$, even more preferably between 22 and 30 $kg/m^3$, in particular between 24 and 28 $kg/m^3$; and/or an air permeability of 1,000 to 8,000 $l/(m^2 sec)$, more preferably from 1,500 to 6,000 $l/(m^2 sec)$, even more preferably from 2,000 to 5,000 $l/(m^2 sec)$, especially preferably from 2,300 to 4,000 $l/(m^2 sec)$ and in particular from 2,400 to 3,300 $l/(m^2 sec)$;
and is preferably obtainable by reaction of a polyisocyanate (i), selected from MDI, PMDI and/or TDI, with a (ii) polyester polyol, which is preferably obtainable by reaction of a dicarboxylic acid with 4 to 8 carbon atoms with a dialcohol with 2 to 6 carbon atoms, whereby the (ii) polyester polyol preferably has a weight average molecular weight of 500 to 4,000 g/mol; and/or
the open-cell polyurethane foam has a proportion of aromatic compounds of 5 to 50%, more preferably from 10 to 45%, in particular from 15 to 40%.

The present invention also comprises any combinations of the cited aspects. Accordingly, an especially preferred foam, for example after three-day storage in bovine serum, has a tensile strength between 155 kPa and 190 kPa; a ductile yield of 260% to 320%; a cell number of 8 to 15 $cm^{-1}$; a raw density between 24 and 28 $kg/m^3$; and/or an air permeability of 2,400 to 3,300 $l/(m^2 sec)$.

This foam is preferably obtainable by reaction of a polyisocyanate (i), selected from MDI, PMDI and/or TDI, with a (ii) polyester polyol, which is preferably obtainable by reaction of a dicarboxylic acid with 4 to 8 carbon atoms with a dialcohol with 2 to 6 carbon atoms, whereby the (ii) polyester polyol preferably has a weight average molecular weight of 500 to 4,000 g/mol.

Furthermore, the invention provides a ready-to-use set for negative pressure wound therapy, including the device in accordance with the present invention, whereby the polyurethane foam is suitable as a wound dressing and is provided in a ready-to-use pack.

The object of the invention is thus a ready-to-use set for negative pressure wound therapy comprising
(a) a cover material for air-tight sealing of the wound space, i.e. the wound and the area surrounding the wound,
(b) as applicable, a means suitable for the connection of a negative pressure source, preferably a means for the functional connection of the wound space with a negative pressure source outside of the cover material in such a way that a negative pressure can be generated in the wound space and fluids can be drawn out of the wound space by suction,
and
(c) a wound dressing in a ready-to-use pack, comprising an open-cell polyurethane foam which has the properties described above, e.g. a tensile strength after three-day storage in bovine serum, measured in accordance with DIN 53571, between 80 kPa and 300 kPa.

The wound dressing (c) included in the set as a ready-to-use pack should preferably be provided in a damp-proof pack. Preferably the ready-to-use wound dressing is provided in sterile form, whereby especially radiation and/or ethylene oxide can be used for sterilization. The set can contain further optional elements such as adhesive means to fix the dressing, sealing means to generate an air-tight seal of the dressing, pressure sensors, connection elements for pressure sensors, additional tubes, connectors for tubes, disinfectants, skin care products, pharmaceutical preparations or instructions for use. The set in accordance with the present invention preferably also contains scissors, pads and/or pincers, in particular in sterile form. Preferably the set also contains a ready-to-use negative pressure unit.

A further object of the invention is the use of the wound dressing (c) explained above for or in the negative pressure wound therapy. An object of the invention is thus also the use of the special open-cell polyurethane foam described above for the negative pressure therapy of wounds, in particular as a wound dressing. In particular, the object of the invention is the use of an open-cell polyurethane foam which has a tensile strength after three days of storage in bovine serum, measured in accordance with DIN 53571, between 80 kPa and 300 kPa for the negative pressure therapy of wounds, in particular as a wound dressing (c). All of the above explanations of preferred embodiments regarding the component (c), i.e. the open-cell polyurethane foam, apply not only to the device in accordance with the present invention, but also to the use of the device in accordance with the present invention.

Special advantages of the device in accordance with the present invention, the set in accordance with the present invention or the use or application in accordance with the present invention, arise when the wounds are burn wounds, wounds caused by mechanical trauma, wounds caused by exposure to chemicals, wounds caused by a metabolic disorder, wounds caused by a circulatory disorder or wounds caused by pressure ulcers, particularly when these wounds are chronic wounds. Furthermore, wounds caused by diabetic foot ulcer can be treated particularly advantageously. In addition, wounds caused by radiation induced ulcer can be treated advantageously with the means of the present invention.

In a further preferred embodiment, the wound dressing (c) is provided for use in negative pressure therapy in the treatment of a wound caused by a skin graft. The application includes the treatment of wounds caused by split-skin and full-skin transplants using negative pressure therapy. Advantageous effects arise due to the structure of the special open-cell polyurethane foam, which preferably has a tensile strength after three days of storage in bovine serum, measured in accordance with DIN 53571, between 80 kPa and 300 kPa, and due to the uniform distribution of pressure. When the wound dressing (c) is used in the treatment of a wound caused by a skin graft, the skin graft can be adequately fixed while avoiding undesired shear forces.

The wound dressing (c) described above can be used advantageously as a wound dressing in the negative pressure therapy of pressure wounds in patients with a body-mass index (BMI=body weight over height squared) of less than 18.0, in particular with a body mass index of 14 to 17.5. This applies in particular to patients aged over 60. The advantageous effect of the device in accordance with the present invention or the set in accordance with the present invention is manifested in particular in such patients.

Another object of the invention is a method for negative pressure wound therapy, comprising the steps of
a) providing a device according to one of the claims 1 to 13;
b) applying the negative pressure dressing to the wound;

c) generating a negative pressure of 25 mm Hg to 250 mm Hg, preferably 50 mm Hg to 150 mm Hg in the wound space for at least 30 minutes and up to a maximum of 7 days, preferably for at least 1 day and up to a maximum of 6 days.

FIGURES

FIG. 1: Schematic view of the device in accordance with the present invention (side view)
1 Wound surroundings (i.e. generally undamaged skin)
2 Air-tight cover material (a)
3 Wound dressing (c)=open-cell polyurethane foam
4 Negative pressure connector (port)
5 Negative pressure connection line
6 Collector
7 Negative pressure unit
8 Wound The device in accordance with the present invention for negative pressure wound therapy is explained in more detail in FIG. 1. FIG. 1 shows a schematic view (side view) of the device in accordance with the present invention. The device comprises an air-tight cover material (2), a means (4-5) for the functional connection of the wound space with a negative pressure source (7) outside of the cover material, and the open-cell foam (3). The cover material (2) is fastened in the area of the wound surroundings (1), usually consisting of undamaged skin. The size of the cover material must be such that the cover material can be fastened outside of the wound space in the area of the wound surroundings (1). The cover material (2) can have different dimensions and shapes, for example circular, oval or rectangular. It can also have an irregular shape matched to the individual wound. The cover material (2) is usually fastened in the area of the wound surroundings (1) and sealed air-tight. This can be achieved, for example, by providing an adhesive edge on the cover material (2). Alternatively, an adhesive substance can be applied either to the edge of the cover material (2) and/or the intact skin around the wound. This has the advantage that it is easier to match the cover material to the shape and size of the wound. In the preferred embodiment shown here, the negative pressure connector (4) is attached to the outside of the air-tight cover material (2) facing away from the wound. In order to functionally connect the wound space with a negative pressure unit (7) outside of the cover material in this arrangement, there must be one or more openings passing through the cover material (2) in the proximity of the negative pressure connector (4).

In a preferred embodiment of the invention the device for the negative pressure wound therapy includes no wound contact layer between the wound dressing (3) and the wound surface (8).

Figure 2:
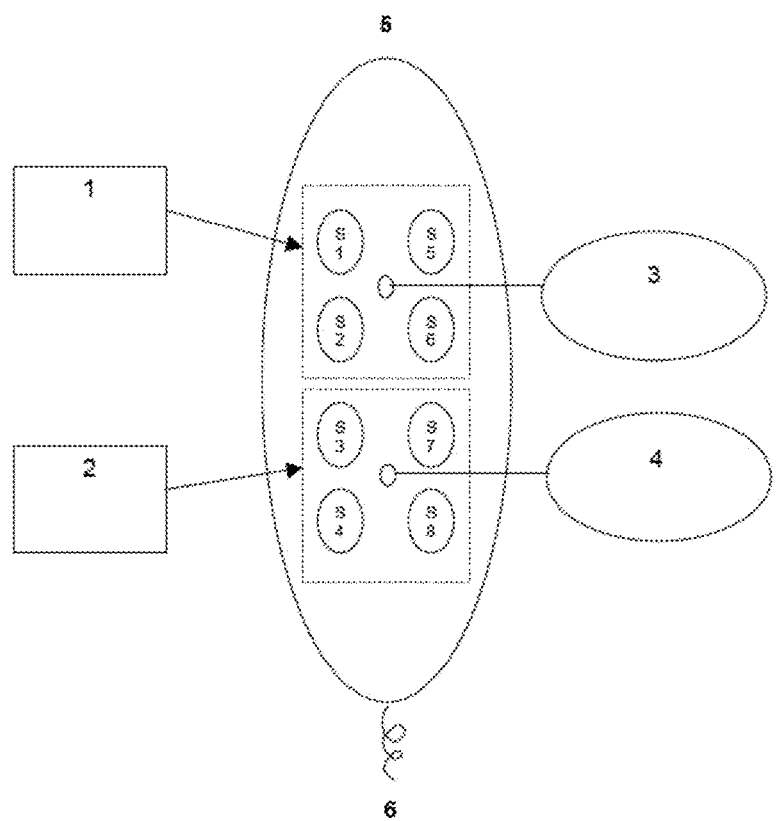
FIG. 2 illustrates the determination of undesired foreign particles in wounds in accordance with Example 2.

FIG. 2 illustrates the determination of undesired foreign particles in wounds in accordance with Example 2.

The invention is illustrated by the following examples.

EXAMPLE 1

Determination of the Tensile Strength

A foam in accordance with the present invention was produced and a foam commercially available for negative pressure therapy was used as a comparison:

Foam A (in accordance with the present invention), obtainable by reaction of polyester polyol and isocyanate, tensile strength after dry storage in a standard climate 160 kPa, tensile strength after three days of storage in bovine serum: 170 kPa.

Foam B (comparison), obtainable by reaction of polyether polyol and isocyanate, tensile strength after dry storage in a standard climate 115 kPa, tensile strength after three days of storage in bovine serum: 72 kPa.

EXAMPLE 2

Determination of Undesired Foreign Particles in Wounds 6 pigs were treated on 8 wounds each with a device for negative pressure wound therapy comprising either the foam A in accordance with the present invention from example 1 or the comparison foam B for 7 days. A systematic diagram of the test set-up is shown in FIG. 2. FIG. 2 shows a pig's back from above. S1 to S8 are the wounds covered with foam, 1 and 2 represent a wound dressing of the foams A or B, each covering four wounds. 3 and 4 are openings for connection with the negative pressure system. 5 is the head of the pig, 6 the tail.

When the treatment period ended, the wounds were examined for undesired foam particles. The result was as follows:

Foam in accordance with the present invention A: 0% of the wounds contained foam particles.

Comparison foam B: 25% of the wounds contained foam particles.

EXAMPLE 3

Histological Examination of Inflammatory Activity in Wounds

As described in Example 2, a foam A according to the present invention and a comparative foam B were used as wound dressings.

Granulation tissues were examined histologically.

Figure 3:
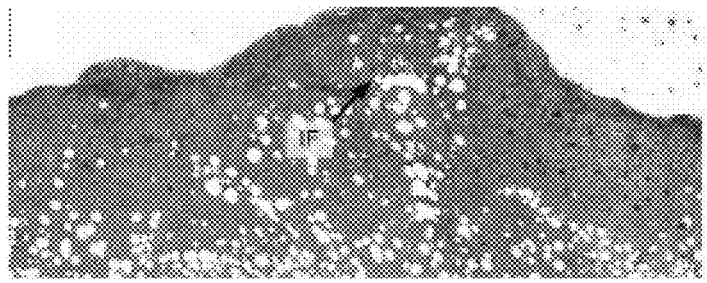
FIGS. 3 and 4 illustrate the histological examination of a wound treated with the inventive foam A showing only little inflammatory foci (IF) and that the inflammatory foci show only minimal neutrophil infiltration.
Figure 4:
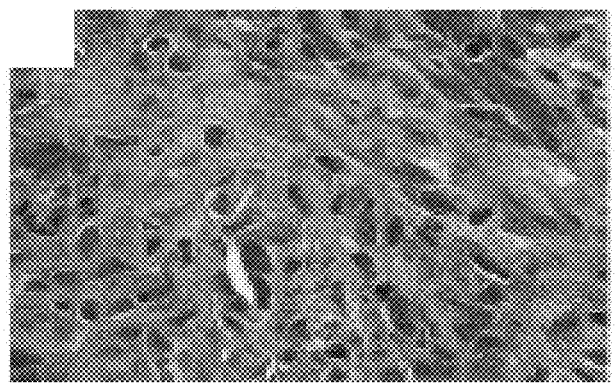

The histological examination of a wound treated with the inventive foam A shows only little inflammatory foci (IF), as illustrated in FIG. 3. The inflammatory foci show only minimal neutrophil infiltration, see FIG. 4.

Figure 5:
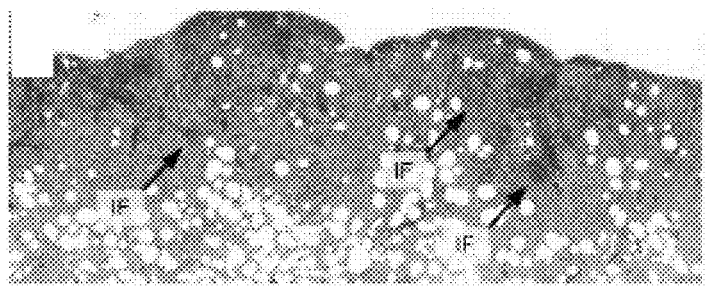
FIGS. 5 and 6 illustrate that there are more areas with inflammatory activity in the granulation tissue of a wound treated with the comparative foam B, and that the inflammatory that the foci (IF) consist of foreign body giant cells, neutrophil granulocytes and lymphocytic cells.
Figure 6:
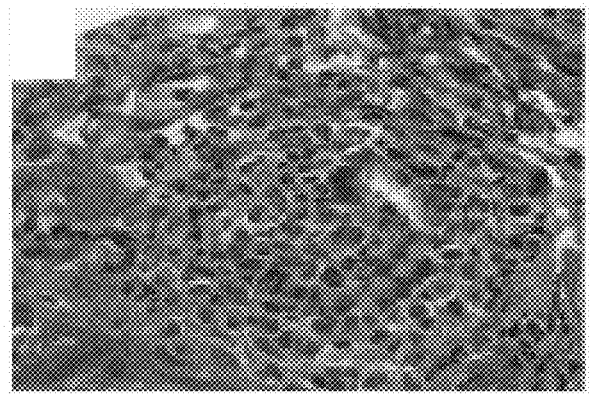

Contrary, there are more areas with inflammatory activity in the granulation tissue of a wound treated with the comparative foam B, as illustrated in FIG. 5. The inflammatory foci (IF) consist of foreign body giant cells, neutrophil granulocytes and lymphocytic cells, as illustrated in FIG. 6.

Consequently, using a foam according to the present invention is associated with less inflammatory activity.

The invention claimed is:
1. A device for negative pressure wound therapy comprising
 (a) a cover material for air-tight sealing of a wound space;
 (b) optionally, a connector of a negative pressure source; and
 (c) an open-cell polyurethane foam as a wound dressing, obtained by reaction of a mixture comprising the components
  (i) polyisocyanate,
  (ii) polyol,
  (iii) blowing agent, and
  (iv) catalyst,
 whereby the open-cell foam, after three days of storage in bovine serum, has a tensile strength, measured in accordance with DIN 53571, between 80 kPa and 300 kPa, and
 whereby the open-cell polyurethane foam has an air permeability of 1,000 to 8,000 l/(m²sec), measured in accordance with DIN EN ISO 9237.

2. The device in accordance with claim 1, whereby the open-cell polyurethane foam has a tensile strength after three days of storage in bovine serum, measured in accordance with DIN 53571, between 150 kPa and 220 kPa.

3. The device in accordance with claim 1, whereby the (i) polyisocyanate is selected from the group consisting of MDI, PMDI and TDI.

4. The device in accordance with claim 1, whereby the (ii) polyol is a polyester polyol obtainable by reaction of a dicarboxylic acid with 4 to 8 carbon atoms with a dialcohol with 2 to 6 carbon atoms.

5. The device in accordance with claim 1, whereby the (ii) polyol is a polyester polyol having a weight average molecular weight of 500 to 4,000 g/mol.

6. A device for negative pressure wound therapy comprising
    (a) a cover material for air-tight sealing of a wound space;
    (b) optionally, a connector of a negative pressure source; and
    (c) an open-cell polyurethane foam as a wound dressing, obtained by reaction of a mixture comprising the components
        (i) polyisocyanate,
        (ii) polyester polyol,
        (iii) blowing agent, and
        (iv) catalyst,
    whereby the open-cell foam, after three days of storage in bovine serum, has a tensile strength, measured in accordance with DIN 53571, between 80 kPa and 300 kPa,
    whereby the open-cell polyurethane foam has a ductile yield of 250% to 650%, measured in accordance with DIN 53571.

7. The device in accordance with claim 1, whereby the open-cell polyurethane foam has a raw density between 15 and 30 kg/m$^3$, measured in accordance with DIN EN ISO 845.

8. The device in accordance with claim 1, whereby the open-cell polyurethane foam has a proportion of aromatic compounds of 5 to 50%.

9. The device in accordance with claim 1, whereby the open-cell polyurethane foam has a hardness of 20 to 70 Shore A, measured in accordance with DIN 53505.

10. The device in accordance with claim 1, whereby the open-cell polyurethane foam has a cell number of 5 to 25 cm$^{-1}$.

11. The device in accordance with claim 1, whereby the open-cell polyurethane foam displays visco-elastic behavior.

12. The device in accordance with claim 1, whereby the cover material (a) has a water vapor permeability of 100 to 2,500 g/m 2×24 h, measured in accordance with DIN EN 13726-2.

13. A method for negative pressure wound therapy, said method comprising
    dressing a wound with an open-cell polyurethane foam obtained by reaction of a mixture comprising the components
        (i) polyisocyanate,
        (ii) polyol,
        (iii) blowing agent, and
        (iv) catalyst,
    wherein the open-cell foam is selected such that after three days of storage in bovine serum it has a tensile strength, measured in accordance with DIN 53571, between 80 kPa and 300 kPa, and wherein the open-cell polyurethane foam has an air permeability of 1,000 to 8,000 l/(m$^2$sec), measured in accordance with DIN EN ISO 9237, and
    applying negative pressure to the wound.

14. The method of claim 13, wherein the wound is a burn wound, a wound caused by mechanical trauma, a wound caused by exposure to chemicals, a wound caused by a metabolic disorder, a wound caused by a circulatory disorder, a wound caused by radiation induced ulcer, a wound caused by diabetic foot ulcer, or a wound caused by pressure ulcer.

15. The method of claim 13, wherein the (ii) polyol is a polyester polyol.

16. The method of claim 13, wherein the (i) polyisocyanate is selected from the group consisting of MDI, PMDI and TDI.

17. The method of claim 15, wherein the (ii) polyester polyol is obtained by reaction of a dicarboxylic acid with 4 to 8 carbon atoms with a dialcohol with 2 to 6 carbon atoms.

18. The device of claim 1, wherein the (ii) polyol is a polyester polyol.

19. The device of claim 18, whereby the open-cell foam, after three days of storage in bovine serum has a tensile strength, measured in accordance with DIN 53571, between 150 kPa and 220 kPa.

20. The device of claim 18, wherein the (i) polyisocyanate is selected from the group consisting of MDI, PMDI and TDI.

* * * * *